US011191941B2

(12) United States Patent
Marquis-Gravel et al.

(10) Patent No.: US 11,191,941 B2
(45) Date of Patent: Dec. 7, 2021

(54) SYSTEMS AND CONNECTORS FOR HEMOSTASIS VALVES AND RELATED METHODS

(71) Applicant: Duke University, Durham, NC (US)

(72) Inventors: Guillaume Marquis-Gravel, Durham, NC (US); Manesh Patel, Durham, NC (US); Katie Carroll, Durham, NC (US); Shweta Shrikant, Morrisville, NC (US)

(73) Assignee: Duke University, Durham, NC (US)

( * ) Notice: Subject to any disclaimer, the term of this patent is extended or adjusted under 35 U.S.C. 154(b) by 129 days.

(21) Appl. No.: 16/401,738

(22) Filed: May 2, 2019

(65) Prior Publication Data
US 2019/0336744 A1 Nov. 7, 2019

Related U.S. Application Data

(60) Provisional application No. 62/666,165, filed on May 3, 2018.

(51) Int. Cl.
*A61M 39/10* (2006.01)
*A61M 25/00* (2006.01)
*A61M 39/06* (2006.01)

(52) U.S. Cl.
CPC ......... *A61M 39/10* (2013.01); *A61M 25/0097* (2013.01); *A61M 2039/062* (2013.01); *A61M 2207/00* (2013.01)

(58) Field of Classification Search
CPC .............. A61M 39/10; A61M 2207/00; A61M 25/0097; A61M 2039/062; A61M 25/0662; A61M 39/0613; A61M 2025/0024; A61M 25/0041; A61M 25/008; A61M 25/0075; A61M 25/0054; A61M 25/0068; A61M 25/01; A61M 25/007; A61M 25/0053; A61M 2025/0079; A61M 39/22; A61M 2025/0681; A61M 2025/0081;
(Continued)

(56) References Cited

U.S. PATENT DOCUMENTS 5,779,681 A 7/1998 Bonn
6,183,443 B1 2/2001 Kratoska et al.
(Continued)

OTHER PUBLICATIONS

Cordis Access Portfolio. Page accessed on Jul. 31, 2019 https://emea.cordis.com/emea/endovascular/lower-extremity-solutions/access.html.
(Continued)

*Primary Examiner* — Bhisma Mehta
*Assistant Examiner* — Robert F Allen
(74) *Attorney, Agent, or Firm* — Olive Law Group, PLLC (57) ABSTRACT

Systems and connectors for hemostasis valves and associated methods are disclosed herein. According to an aspect, a connector for a medical device includes a body defining a first opening, a second opening, and a channel. The channel provides passage between the first opening and the second opening. The body is configured to engage an inlet port of a hemostasis valve at the first opening when the body and the hemostasis valve are arranged in one or more positions with respect to each other. The connector also includes a clip attached to the body and configured to fasten the body to the hemostasis valve when the body and the hemostasis valve are arranged in one of the positions.

15 Claims, 6 Drawing Sheets

(58) Field of Classification Search
CPC .......... A61M 2025/0076; A61M 39/06; A61M 2039/1077; A61M 2039/1094; A61M 39/12; A61M 25/0014; A61B 17/3462; A61B 17/3498; A61B 17/3439; A61B 2017/00867; Y10T 137/87917; A61F 2/95
See application file for complete search history.

(56) References Cited

U.S. PATENT DOCUMENTS

| | | | |
|---|---|---|---|
| 6,355,026 | B1 | 3/2002 | Mick |
| 10,758,721 | B2* | 9/2020 | Sonderegger ....... A61M 5/3213 |
| 10,842,981 | B2* | 11/2020 | Agrawal ........... A61M 39/0613 |
| 2005/0010238 | A1* | 1/2005 | Potter ............... A61M 39/0606 606/129 |
| 2010/0007134 | A1* | 1/2010 | Elton .................... F16L 37/248 285/31 |
| 2010/0100055 | A1 | 4/2010 | Mustapha |
| 2018/0256875 | A1* | 9/2018 | Agrawal ............... A61M 39/06 |
| 2019/0105484 | A1* | 4/2019 | Doorn ................. A61J 15/0026 |
| 2019/0167967 | A1* | 6/2019 | Mottola ............ A61M 39/0693 |

OTHER PUBLICATIONS

Food and Drug Administration "510(k) Clearances" Accessed: Jul. 26, 2019 (one (1) page) https://www.fda.gov/medical-devices/device-approvals-denials-and-clearances/510k-clearances.

Fornell, Dave. 2016 "Radial Access Adoption in the United States" Diagnostic and Interventional Cardiology. Published May 27, 2016 (four (4) pages).

Joshi, Bhavna .2016 "Cardiovascular Surgical Devices: Technologies and Global Markets" BCC Research, Sep. 2016.

Laxmi, Vijay 2017 "Medical Devices: Technologies and Global Markets" BCC Research. Jan. 2017.

Muhammad Asrar ul Haq et al. 2016. "Prevalence and outcomes of trans-radial access for percutaneous coronary intervention in contemporary practise" International Journal of Cardiology vol. 221 (2016) pp. 264-268.

Pancholy, Samir, B. et al. 2015 "Effect of Vascular Access Site Choice on Radiation Exposure During Coronary Angiography" The REVERE Trial (Randomized Evaluation of Vascular Entry Site and Radiation Exposure) Journal of the American College of Cardiology. vol 8. Issue 9 (eight (8) pages).

Sciahbasi, A. et al. 2017. "Radiation Exposure and Vascular Access in Acute Coronary Syndromes. The RAD-Matrix Trial" Journal of the American College of Cardiology. Radiation Exposure and PCI. vol. 69, Issue 20 http://dx.doi.org/10.1016/j.jacc.2017.03.018 (eight (8) pages).

Shah, Rachit, M. 2016. "Comparison of Transradial Coronary Procedures via Right Radial Versus Left Radial Artery Approach: A Meta-Analysis" Catheterization and Cardiovascular Interventions DOI: 10.1002/ccd.26519 (eight (8) pages).

Terumo Interventional Systems: Access. Page Accessed on Jul. 31, 2019 http://www.terumois.com/products/access.html.

* cited by examiner

SYSTEMS AND CONNECTORS FOR HEMOSTASIS VALVES AND RELATED METHODS

CROSS REFERENCE TO RELATED APPLICATION

This application claims priority to U.S. Patent Application No. 62/666,165, filed May 3, 2018, and titled LONG EXTRA-CORPOREAL ARTERIAL SHEATHS AND CATHETERS FOR CORONARY ANGIOGRAPHY AND INTERVENTON AND METHODS OF USING SAME, the content of which is incorporated herein by reference in its entirety.

TECHNICAL FIELD

The presently disclosed subject matter relates generally to medical equipment. Particularly, the presently disclosed subject matter relates to systems and connectors for hemostasis valves.

BACKGROUND

Coronary angiograms and percutaneous coronary intervention (PCI) are medical procedures that involve access to the arterial system through the radial (i.e., wrist) or the femoral (i.e., groin) arteries. Once the arteries are accessed, an operator inserts a sheath in the artery up to the skin level, which stays in place during the procedure. Equipment needed to perform the angiography (e.g., wires and diagnostic catheters) or the PCI (e.g., guiding catheters) pass through the sheath.

During the angiography or PCI, the operator is typically positioned on the right side of the patient and manipulates equipment outside of the body and at the level of the sheath. In some instances, the procedure must be performed on the left radial or femoral artery. In such instances, the operator, positioned on the right side of the patient, must bend over the patient to perform the procedure. However, procedures using a left-sided arterial access raise concerns for patient discomfort, operator discomfort, and radiation safety issues for the operator. For at least these reasons, there is a need for medical equipment and techniques that reduce or eliminate these issues.

BRIEF DESCRIPTION OF THE DRAWINGS

Having thus described the presently disclosed subject matter in general terms, reference will now be made to the accompanying Drawings, which are not necessarily drawn to scale, and wherein:

SUMMARY

The presently disclosed subject matter includes systems and connectors for hemostasis valves and associated methods. According to an aspect, a connector for a medical device includes a body defining a first opening, a second opening, and a channel. The channel provides passage between the first opening and the second opening. The body is configured to engage an inlet port of a hemostasis valve at the first opening when the body and the hemostasis valve are arranged in one or more positions with respect to each other. The connector also includes a clip attached to the body and configured to fasten the body to the hemostasis valve when the body and the hemostasis valve are arranged in one of the positions.

According to another aspect, a system includes a sheath comprising a first hemostasis valve having an inlet port. The system also includes a connector including a body that defines a first opening, a second opening, and a channel. The channel provides passage between the first opening and the second opening. The body is configured to engage the inlet port of the first hemostasis valve at the first opening when the body and the first hemostasis valve are arranged in one or more positions with respect to each other. The connector includes a clip attached to the body and configured to fasten the body to the first hemostasis valve when the body and the first hemostasis valve are arranged in one of the positions. The system also includes a second hemostasis valve and a tube. The tube provides another channel that operably connects the second hemostasis valve and the channel defined by the body.

According to another aspect, a method includes providing a system. The system includes connector having a body that defines a first opening, a second opening, and a channel. The channel provides passage between the first opening and the second opening. The connector also includes a clip attached to the body and configured to fasten the body to the first hemostasis valve when the body and the first hemostasis valve are arranged in a position. The system also includes a second hemostasis valve and a tube that provides another channel that operably connects the second hemostasis valve and the channel defined by the body. Further, the method includes arranging the body and the first hemostasis valve in the position with respect to each other such that the body engages the inlet port of the first hemostasis valve at the first opening and such that the clip fastens the body to the first hemostasis valve.

DETAILED DESCRIPTION

The following detailed description is made with reference to the figures. Exemplary embodiments are described to illustrate the disclosure, not to limit its scope, which is defined by the claims. Those of ordinary skill in the art will recognize a number of equivalent variations in the description that follows.

Articles "a" and "an" are used herein to refer to one or to more than one (i.e. at least one) of the grammatical object of the article. By way of example, "an element" means at least one element and can include more than one element.

"About" is used to provide flexibility to a numerical endpoint by providing that a given value may be "slightly above" or "slightly below" the endpoint without affecting the desired result.

The use herein of the terms "including," "comprising," or "having," and variations thereof is meant to encompass the elements listed thereafter and equivalents thereof as well as additional elements. Embodiments recited as "including," "comprising," or "having" certain elements are also contemplated as "consisting essentially of" and "consisting" of those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a range is stated as between 1%-50%, it is intended that values such as between 2%-40%, 10%-30%, or 1%-3%, etc. are expressly enumerated in this specification. These are only examples of what is specifically intended, and all possible combinations of numerical values between and including the lowest value and the highest value enumerated are to be considered to be expressly stated in this disclosure.

Unless otherwise defined, all technical terms used herein have the same meaning as commonly understood by one of ordinary skill in the art to which this disclosure belongs.

As used herein, the term "subject" and "patient" are used interchangeably herein and refer to both human and nonhuman animals. The term "nonhuman" animals" of the disclosure include all vertebrates, e.g., mammals and non-mammals, such as nonhuman primates, sheep, dog, cat, horse, cow, chickens, amphibians, reptiles, and the like.

Figure 1:
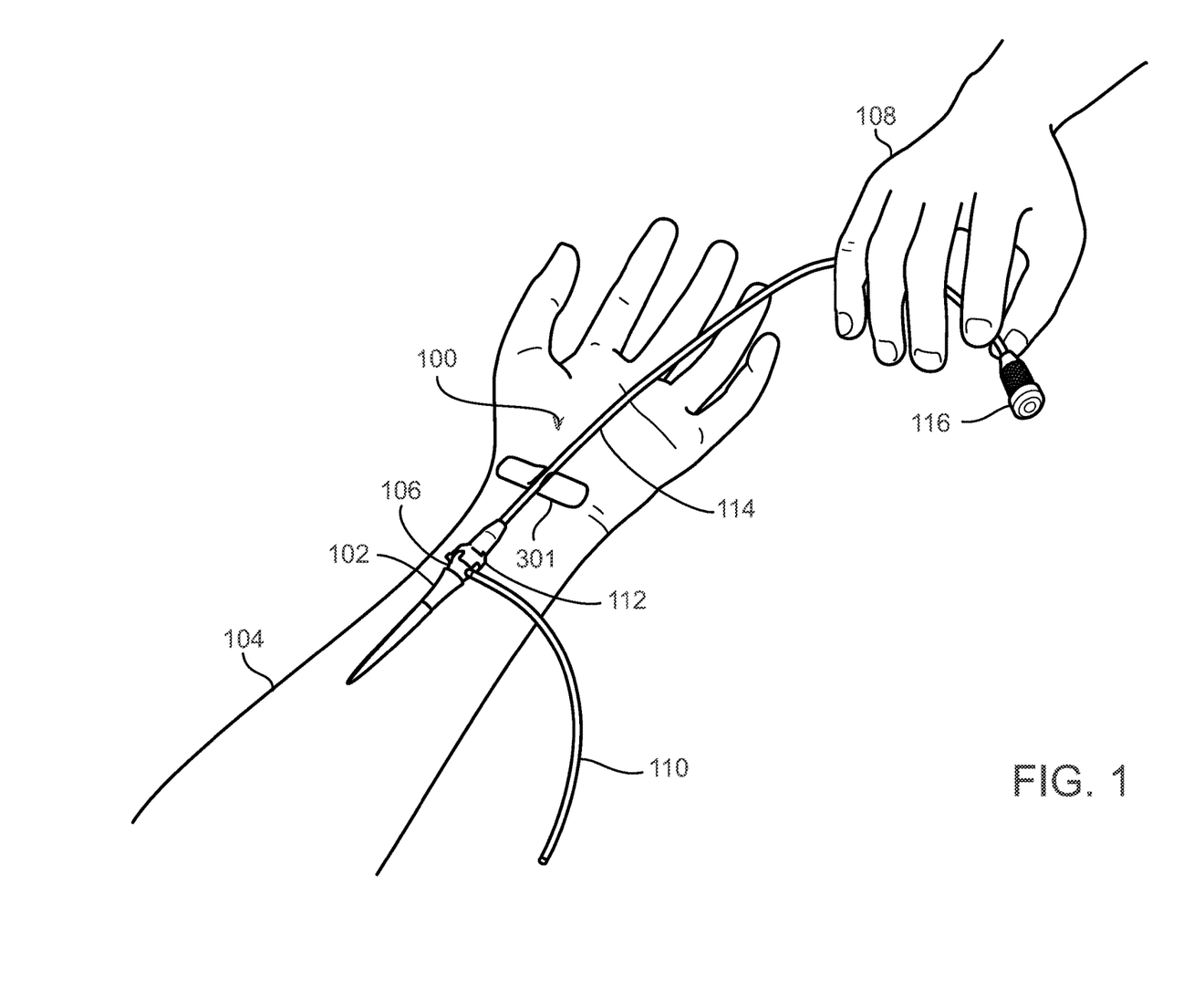
FIG. 1 is a perspective view of an example system for extending access to a sheath in use with a patient in accordance with embodiments of the present disclosure.

FIG. 1 illustrates a perspective view of an example system 100 for extending access to a sheath 102 in use with a patient 104 in accordance with embodiments of the present disclosure. Referring to FIG. 1, the sheath 102 is inserted into an arm of the patient 104. Particularly, the sheath 102 is inserted into an aortic passageway in the left arm of the patient 104 to thereby provide access to the patient's coronary vasculature as will be understood by those of skill in the art. In this example, the sheath 102 is inserted to access the coronary vasculature through the patient's 104 wrist, although it should be understood that alternatively the sheath 102 along with the system 100 may be used to access a patient's arterial system through the femoral arteries or other suitable location. The sheath 102 may be inserted a suitable distance into the patient's 104 vasculature (e.g., between about 5 and 10 centimeters). The portion of the sheath 102 inside the body of the patient 104 may be made of a suitable material and have a suitable length. A colored or other suitable mark on the sheath 102 may show the demarcation between the intra- and extra-corporeal segments of the sheath 102.

The sheath 102 includes a hemostasis valve 106 by which a medical practitioner 108 can insert equipment to perform an angiogram or coronary intervention on the patient 104. For example, equipment such as wires, diagnostic catheters, or guiding catheters may be inserted into the hemostasis valve 106 for performing a procedure. The sheath 102 includes a drain tube 110 for removing excess fluid or to inject drugs.

The system 100 includes a connector 112, a tube 114, and hemostasis valve 116 assembled together and operably attached to the sheath 102 as shown to provide an extension to the sheath 102 such that it is more easily reached and used by the medical practitioner 108. In this way, the system 100 can be used in a left-sided arterial access procedure to reduce patient discomfort, to reduce operator discomfort, and to reduce radiation exposure for medical practitioners. The connector 112 is attached to an end of the tube 114, and the hemostasis valve 116 is attached to an opposing end of the tube 114 such that a channel is defined that extends from one opening at the hemostasis valve 116 to another opening at the connector 112. In this way, the use of and access to the sheath 102 at the hemostasis valve 106 is extended to the hemostasis valve 116. The connector 112 may be made of, for example, a polymer, polycarbonate, PTFE, PP, nylon, or acrylonitrile butadiene styrene (ABS) material.

Figure 2A:
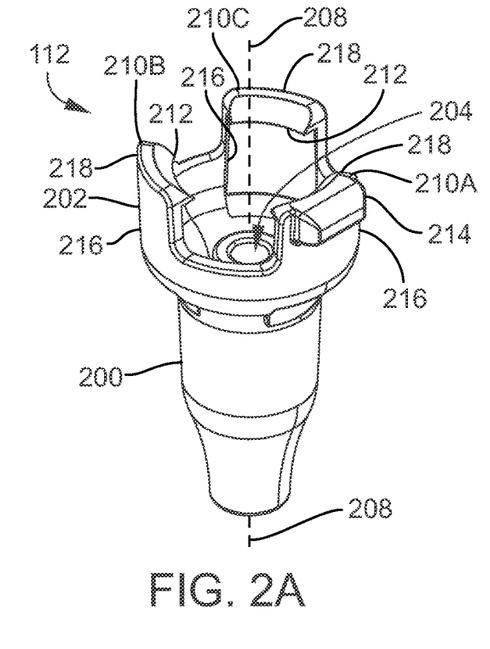
FIGS. 2A-2F are different views of the connector shown in FIG. 1 in accordance with embodiments of the present disclosure.
Figure 2B:
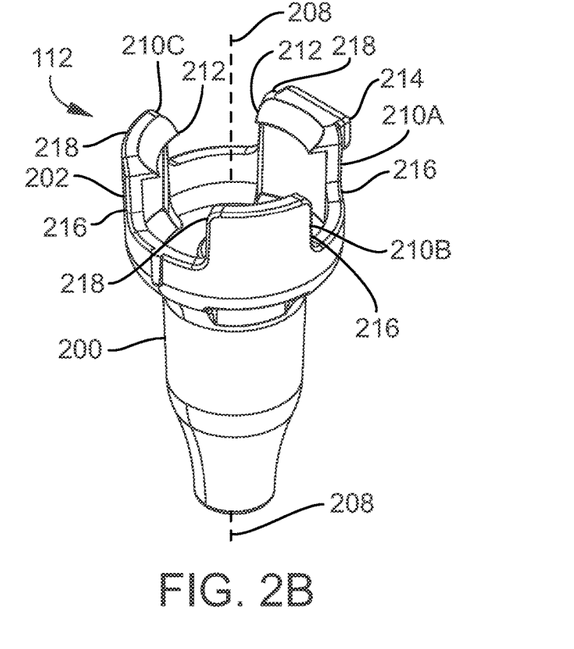
Figure 2C:
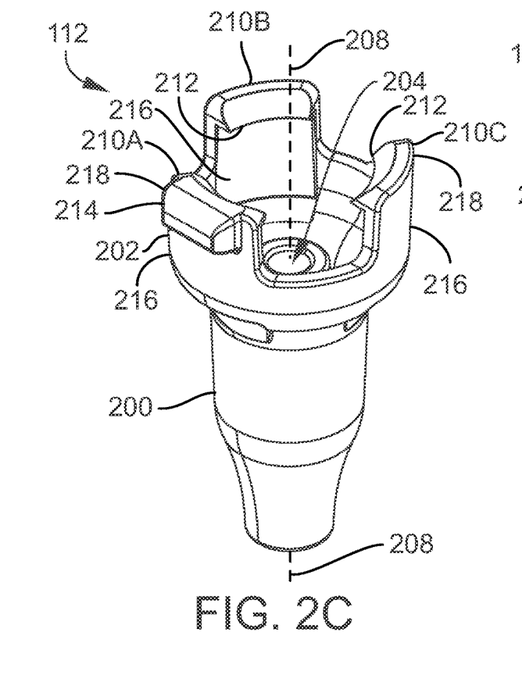
Figure 2D:
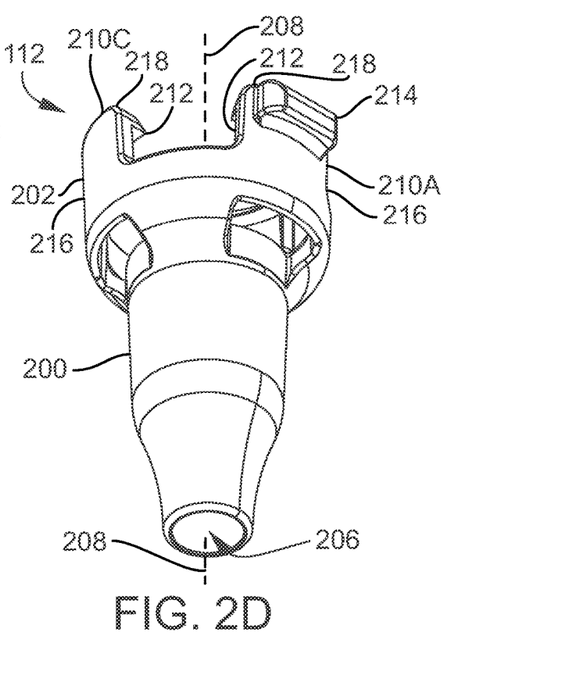

FIGS. 2A-2F illustrate different views of the connector 112 shown in FIG. 1 in accordance with embodiments of the present disclosure. Particularly, FIGS. 2A, 2B, and 2C are top perspective views of the connector 112 from different angles. FIG. 2D is a bottom perspective view of the connector 112. Referring to FIGS. 2A, 2B, and 2C, the connector 112 includes a body 200 and a clip 202. The body 200 defines an opening 204 (shown in FIGS. 2A and 2C) and an opening 206 (shown in FIG. 2D). The body 200 also defines a channel (not shown) that extends between the openings 204 and 206 for providing passage therebetween. In this example, channel is cylindrical in shape and has a diameter that is the same as the openings 204 and 206.

The body 200 is configured to engage an inlet port of a hemostasis valve at the opening 204 when the body 200 and the hemostasis valve are arranged in one or more positions with respect to each other. For example, the channel of the body 200 extends along an axis indicated by broken line 208. The body 200 and the hemostasis valve may engage at the opening 204 in this example at any angle orientation of the body 200 and hemostasis valve about the axis 208. The body 200 defines a rigid encircling the opening 204 to fit to the corresponding opening or inlet of the hemostasis valve. In this example, the body 200 tapers towards the opening 206, but may alternatively be any other suitable shape and size.

The clip 202 is attached to the body 200 and configured to fasten the body 200 to the hemostasis valve when the body 200 and the hemostasis valve are arranged as shown in FIG. 1 or in any of the aforementioned angle orientation about the axis 208. In this position, the channel defined by the body 200 aligns with a channel defined in the interior of the hemostasis valve. Further, the opening 208 may be attached to a tube (e.g., the tube 114 shown in FIG. 1) such that a passageway is formed between an interior of the tube and the inlet of the hemostasis valve.

The clip 202 includes multiple spaced-apart arms 210A, 210B, and 210C. The arms 210A, 210B, and 210C can together or separately attach the body 200 to the inlet of the hemostasis valve such that the opening 204 engages the inlet. Each arm 210A, 210B, and 210C may include a finger 212 for grasping to one or more features on the hemostasis valve. Arm 210A defines a protrusion 214 that extends away from the body 200 for gripping by a person to release the arms 210A, 210B, and 210C from grasping the feature(s) on the hemostasis valve to thereby release the connector 112 from the hemostasis valve. By pulling the protrusion 214, the arm 210A can be deflected outward to release the connector 112 from the hemostasis valve. Thus, the connector 112 can be removably fastened to hemostasis valve.

The arms 210A, 210B, and 210C each include a proximal end 216 and a distal end 218. The arms 210A, 210B, and 210C are each attached to the body 200 at their respective proximal end 216 such that the arms substantially surround the opening 204. Further, the distal end 218 of each arm extends away from the body 200 and beyond the opening 204 such that the hemostasis valve is held by the arms when the body 200 and the hemostasis valve are in position for engagement. The arms 210A, 210B, and 210C are each flexible at their respective proximal end 216 for movement of their respective distal end 218 when force is applied to their respective distal end 218. For example, when the hemostasis valve is positioned to engage with the connector 112, the distal ends 218 are deflected outward by the hemostasis valve and subsequently the fingers 212 grasp the hemostasis valve when in operational position.

Figure 2E:
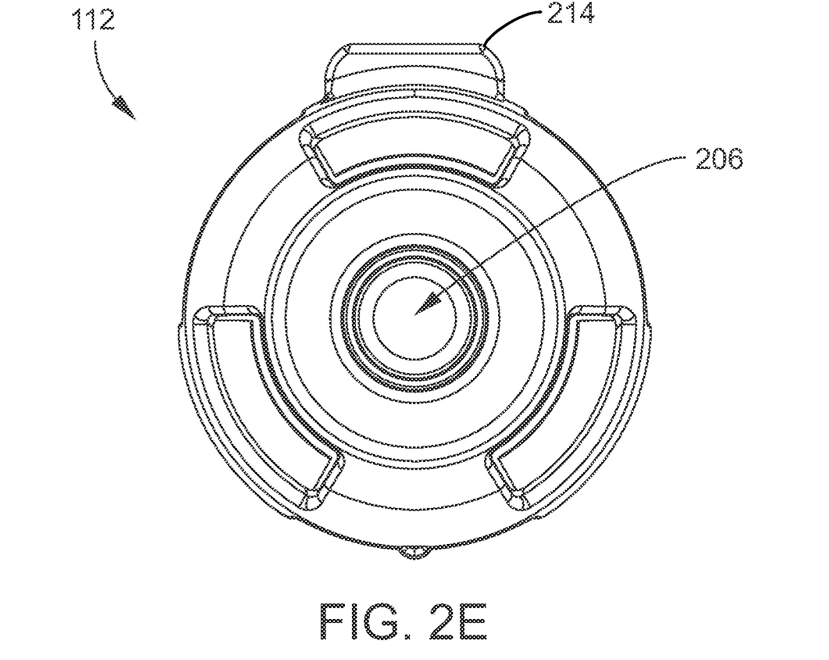
Figure 2F:
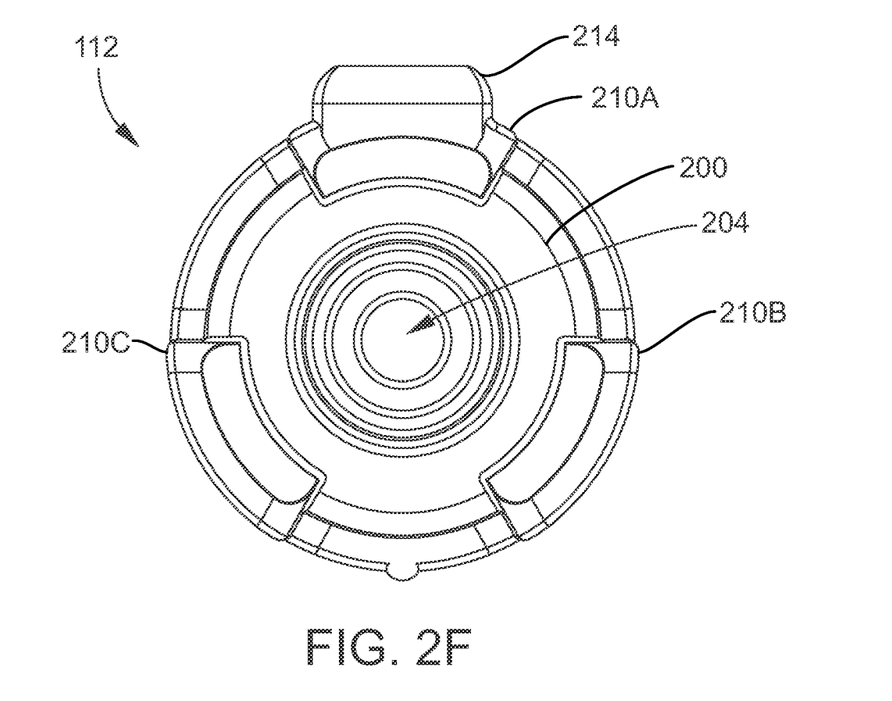

FIGS. 2E and 2F are opposing ends views of the connector 112 shown in FIGS. 2A-2D. Particularly, FIG. 2E shows the end with opening 206, and FIG. 2F shows the end with opening 204.

Figure 3A:
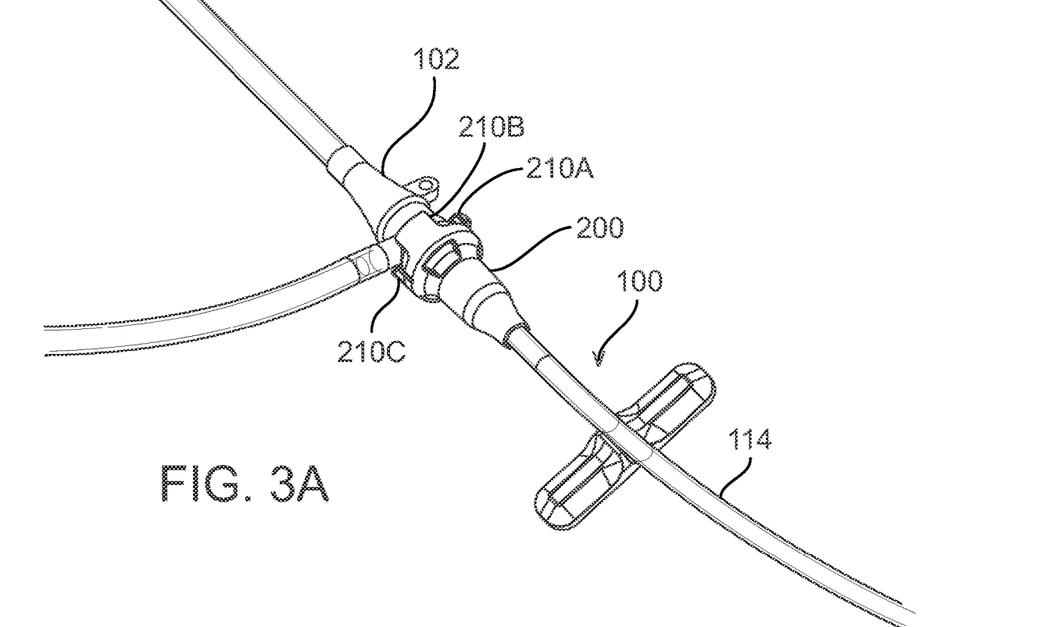
FIGS. 3A-3F are different views showing close-ups of the system operably engaged with the sheath in accordance with embodiments of the present disclosure.

FIGS. 3A-3F illustrate different views showing close-ups of the system 100 operably engaged with the sheath 102. Referring to FIG. 3A, the figure is a perspective view of the system 100 and sheath 102. The system 100 includes an adhesive component 301 that is attached to the tube 114 and has a side for adhering the adhesive component 301 along with the tube 114 to the patient's arm as shown in FIG. 1.

Figure 3B:
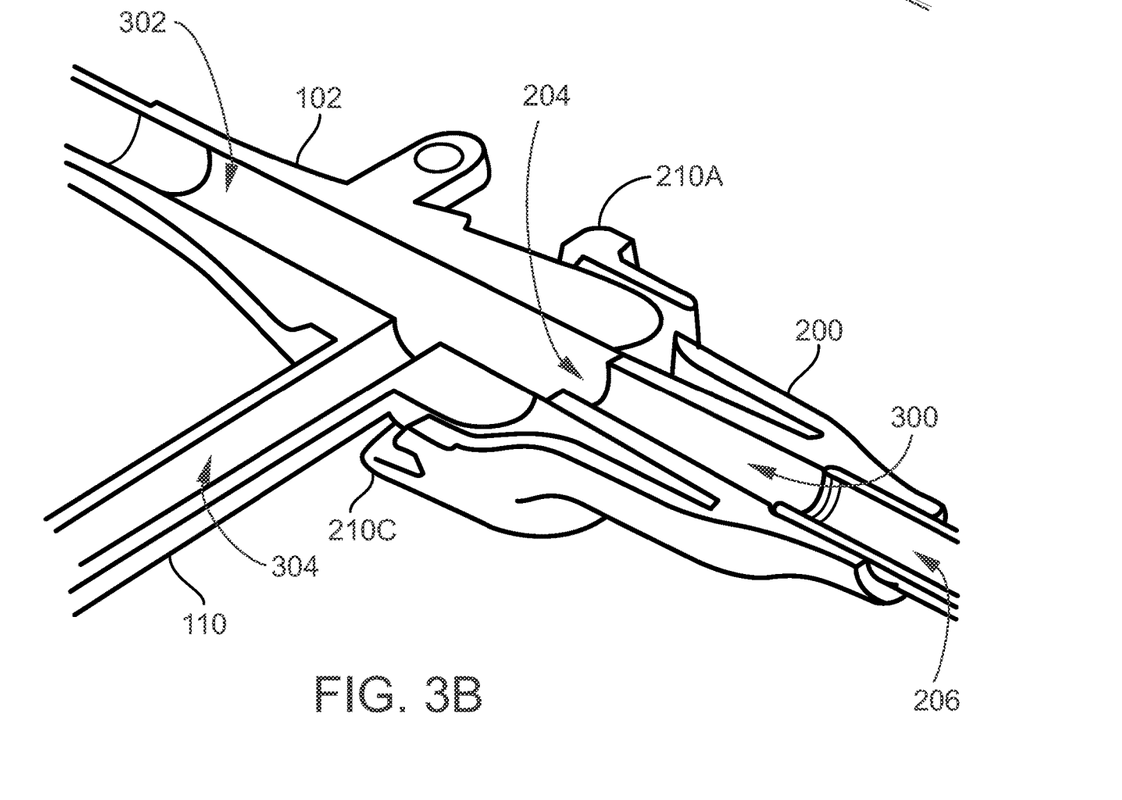

FIG. 3B shows a cross-sectional view of the system 100 operably engaged with the sheath 102. Referring to FIG. 3B, a channel 300 that extends between the openings 204 and 206 is shown. In this example, the channel 300 is coaxial with a channel 302 of the sheath 102. The figure also shows that a channel 304 of the tube 110 fluidly connects with the channels 300 and 302.

Figure 3C:
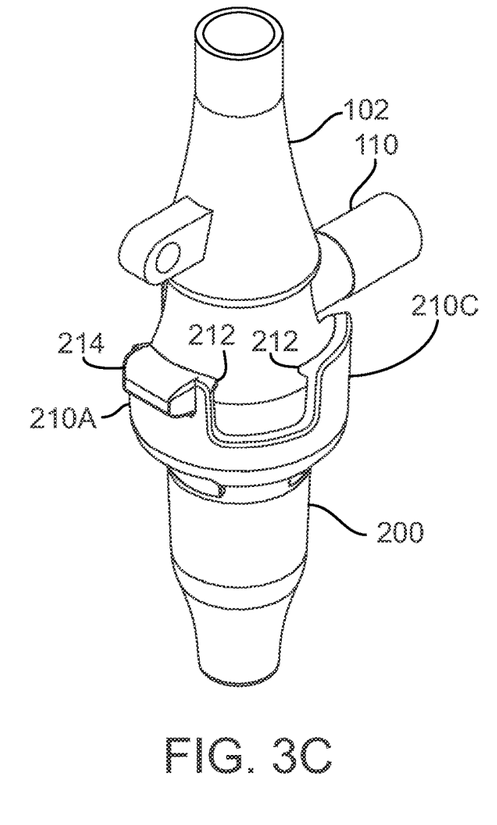
Figure 3D:
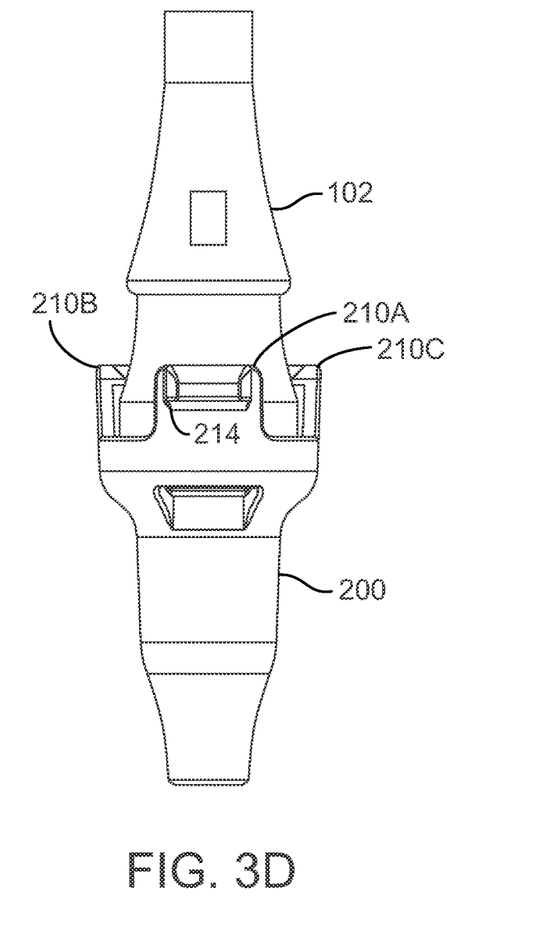
Figure 3E:
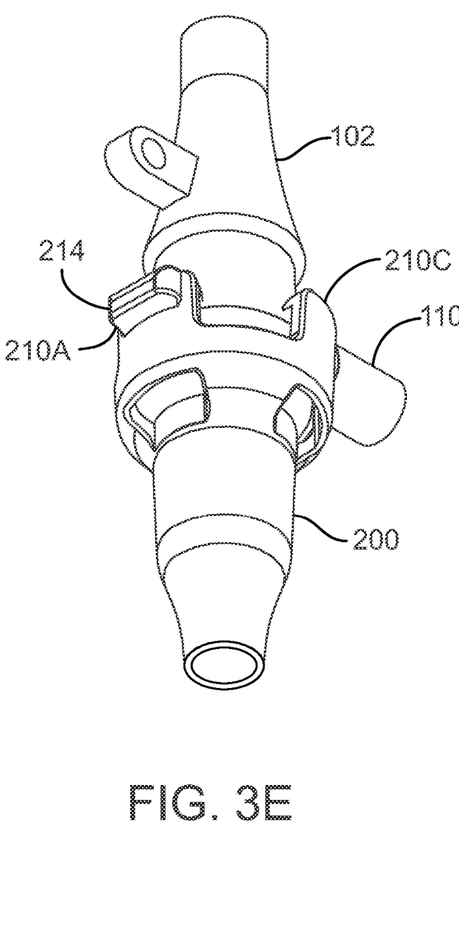
Figure 3F:
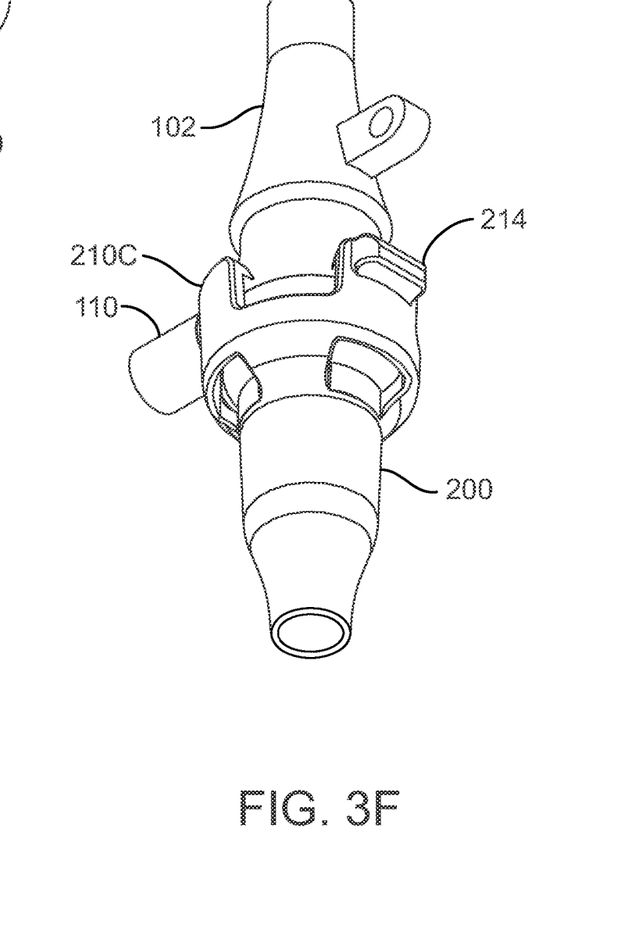

FIGS. 3C and 3D are a top perspective view and a side view of the system 100 operably engaged with the sheath 102. FIGS. 3E and 3F are bottom perspective views of the system 100 operably engaged with the sheath 102 from different angles.

In accordance with embodiments, the system disclosed herein (e.g., system 100) functions as a sheath for providing access to a patient's coronary vasculature through an aortic passageway leading from an iliac, femoral, or radial location. Particularly, the tube 114 may function as an axially elongated sheath tube with a lumen extending between the ends of the tube 114. The tube 114 may have a length of between about 30 centimeters and 50 centimeters or any other suitable length. Further, the tube 114 may be flexible and bend at an angle of at least 30 degrees. In another example, the tube 114 may be configured to bend or curve to the right side at an angle of between 30 and 50 degrees. A guidewire and/or catheter may be provided having the same or similar length and curvature for functioning with the system 100.

In accordance with embodiments, a method of performing a percutaneous procedure in a patient's vasculature system includes performing a surgical cutdown or percutaneous access to the iliac or femoral artery of the patient's vasculature. The method also includes advancing a distal end of a catheter as disclosed herein into an iliac or femoral artery to the desired location within the patient's vasculature. Further, the method includes performing therapy or diagnosis through the expanded distal portion of the sheath by way of at least one catheter inserted through the sheath. Further, the method includes removing the catheter(s) from the sheath and removing the sheath from the vascular system.

In an example of the percutaneous procedure, an entry needle may be placed into the artery and a guidewire inserted through the cannula of the needle into the artery in order to insert a vascular sheath. After insertion of the guidewire, the entry needle may be removed and the dilator and sheath slid along the guidewire into the artery. The dilator may assist with maintaining the structure of the sheath while inserting. After the sheath has been fully inserted, both the dilator and the guidewire may be removed. The operator can flush the sheath with heparinized saline. The sheath may stay in place for the duration of the procedure. All equipment to perform an angiogram (e.g., wires and diagnostic catheters) and/or percutaneous coronary intervention (e.g., guiding catheters) may pass through the sheath. A catherization lab may be set up so that the operator is positioned on the right side of the patient. There may be a lead shield placed between the operator and the x-ray. The operator may manipulate the catheters outside the body at the level of the sheath, where the left hand is on the hub of the sheath and their right hand is feeding a catheter through the sheath. The operator both pushes and pulls the catheter through the hub, as well as torquing the catheter.

While the embodiments have been described in connection with the various embodiments of the various figures, it is to be understood that other similar embodiments may be used, or modifications and additions may be made to the described embodiment for performing the same function without deviating therefrom. Therefore, the disclosed embodiments should not be limited to any single embodiment, but rather should be construed in breadth and scope in accordance with the appended claims.

What is claimed is:

1. A connector for a medical device, the connector comprising:
a body defining a first opening, a second opening, and a channel, wherein the channel provides passage between the first opening and the second opening, and wherein the body is configured to engage an inlet port of a hemostasis valve at the first opening when the body and the hemostasis valve are arranged in at least one position with respect to each other; and
a clip attached to the body and comprising three arms disposed around the first opening for holding to sides of the hemostasis valve when the body and the hemostasis valve are arranged in the at least one position, wherein the three arms each define a finger for grasping to a feature on the hemostasis valve to hold the clip to the hemostasis valve when the body and the hemostasis valve are arranged in the at least one position,
wherein each of the three arms includes a proximal end and a distal end, wherein the three arms are each flexible at the proximal end for movement of their respective distal end when force is applied to their respective distal end, and
wherein one of the three arms comprises a protrusion that extends away from the finger for releasing the finger from the hemostasis valve upon outward deflection of the protrusion.

2. The connector of claim 1, wherein the channel of the body aligns with a channel of the hemostasis valve when the body and the hemostasis valve are arranged in the at least one position.

3. The connector of claim 1, wherein the second opening is configured to attach to a tube such that a passageway is formed between an interior of the tube and the inlet port of the hemostasis valve.

4. The connector of claim 1, wherein the body comprises a polymer, polycarbonate, PTFE, PP, nylon, or acrylonitrile butadiene styrene (ABS) material.

5. The connector of claim 1, wherein the three arms are each attached to the body at their respective proximal end such that the three arms substantially surround the first opening, and wherein the distal end of each arm extends away from the body and beyond the first opening such that the hemostasis valve is held by the three arms when the body and the hemostasis valve are arranged in the at least one position.

6. The connector of claim 1, wherein the three arms are each attached to the body at their respective proximal end such that the three arms substantially surround the first opening.

7. The connector of claim 1, wherein the clip is configured to removably fasten the body to the hemostasis valve when the body and the hemostasis valve are arranged in the at least one position.

8. The connector of claim 1, wherein the hemostasis valve is a first hemostasis valve, and
wherein the connector further comprises a second hemostasis valve and a tube, wherein the tube provides another channel that operably connects the second hemostasis valve and the channel defined by the body.

9. A system comprising:
a sheath comprising a first hemostasis valve including an inlet port;
a connector comprising:
a body defining a first opening, a second opening, and a channel, wherein the channel provides passage between the first opening and the second opening, wherein the body is configured to engage the inlet port of the first hemostasis valve at the first opening when the body and the first hemostasis valve are arranged in at least one position with respect to each other; and
a clip attached to the body and comprising three arms disposed around the first opening for holding to sides of the first hemostasis valve when the body and the first hemostasis valve are arranged in the at least one position, wherein the three arms each define a finger for grasping to a feature on the first hemostasis valve to hold the clip to the first hemostasis valve when the body and the first hemostasis valve are arranged in the at least one position,
wherein each of the three arms includes a proximal end and a distal end, wherein the three arms are each flexible at the proximal end for movement of their respective distal end when force is applied to their respective distal end, and
wherein one of the three arms comprises a protrusion that extends away from the finger for releasing the finger from the first hemostasis valve upon outward deflection of the protrusion; and
a second hemostasis valve and a tube, wherein the tube provides another channel that operably connects the second hemostasis valve and the channel defined by the body.

10. The system of claim 9, wherein the channel of the body aligns with a channel of the first hemostasis valve when the body and the first hemostasis valve are arranged in the at least one position.

11. The system of claim 9, wherein the body comprises one of a polymer, polycarbonate, PTFE, PP, nylon, or acrylonitrile butadiene styrene (ABS) material.

12. The system of claim 9, wherein the three arms are each attached to the body at their respective proximal end such that the three arms substantially surround the first opening, and wherein the distal end of each arm extends away from the body and beyond the first opening such that the first hemostasis valve is held by the three arms when the body and the first hemostasis valve are arranged in the at least one position.

13. The system of claim 9, wherein the three arms are each attached to the body at their respective proximal end such that the three arms substantially surround the first opening.

14. The system of claim 9, wherein the clip is configured to removably fasten the body to the first hemostasis valve when the body and the first hemostasis valve are arranged in the at least one position.

15. A method comprising:
providing a system comprising:
a connector comprising:
a body defining a first opening, a second opening, and a channel, wherein the channel provides passage between the first opening and the second opening;
a clip attached to the body and comprising three arms disposed around the first opening for holding to sides of a first hemostasis valve when the body and the first hemostasis valve are arranged in a position, wherein the three arms each define a finger for grasping to a feature on the first hemostasis valve to hold the clip to the first hemostasis valve when the body and the first hemostasis valve are arranged in the position,
wherein each of the three arms includes a proximal end and a distal end, wherein the three arms are each flexible at the proximal end for movement of their respective distal end when force is applied to their respective distal end, and
wherein one of the three arms comprises a protrusion that extends away from the finger for releasing the finger from the first hemostasis valve upon outward deflection of the protrusion;
a second hemostasis valve; and
a tube that provides another channel that operably connects the second hemostasis valve and the channel defined by the body; and
arranging the body and the first hemostasis valve in the position with respect to each other such that the body engages an inlet port of the first hemostasis valve at the first opening and such that the clip fastens the body to the first hemostasis valve.

\* \* \* \* \*